(12) United States Patent
Lin (10) Patent No.: US 11,684,741 B2
(45) Date of Patent: Jun. 27, 2023

(54) BREATHING MASK

(71) Applicant: Ming-Hsien Lin, Kaohsiung (TW)

(72) Inventor: Ming-Hsien Lin, Kaohsiung (TW)

( * ) Notice: Subject to any disclaimer, the term of this patent is extended or adjusted under 35 U.S.C. 154(b) by 560 days.

(21) Appl. No.: 16/860,321

(22) Filed: Apr. 28, 2020

(65) Prior Publication Data

US 2020/0398012 A1 Dec. 24, 2020

(30) Foreign Application Priority Data

Jun. 18, 2019 (TW) .................. 108121081

(51) Int. Cl.
*A61M 16/06* (2006.01)
*A61M 16/10* (2006.01)
*A61M 16/20* (2006.01)

(52) U.S. Cl.
CPC .... *A61M 16/0605* (2014.02); *A61M 16/0683* (2013.01); *A61M 16/1065* (2014.02); *A61M 16/208* (2013.01); *A61M 2202/0208* (2013.01); *A61M 2205/8206* (2013.01)

(58) Field of Classification Search
CPC .......... A61M 16/0605; A61M 16/0683; A61M 16/1065; A61M 16/208; A61M 2202/0208; A61M 2205/8206; A62B 7/08; A62B 18/08; A62B 18/025; A62B 7/00–14; A62B 18/00–10; A62B 21/00; C01B 13/02–0207

USPC .......................................... 423/579
See application file for complete search history.

(56) References Cited

U.S. PATENT DOCUMENTS

2009/0250060 A1* 10/2009 Hacke ................... A61M 16/06
 128/205.12
2020/0038614 A1* 2/2020 Duff .................. A61M 16/0066

FOREIGN PATENT DOCUMENTS

CN 106235472 A * 12/2016

OTHER PUBLICATIONS

Machine Translation of CN 106235472 A, Accessed Oct. 28, 2022 (Year: 2022).*

* cited by examiner

*Primary Examiner* — Elliot S Ruddie
(74) *Attorney, Agent, or Firm* — Leong C. Lei (57) ABSTRACT

A breathing mask includes a mask body unit and a container. The mask body unit includes a mask body having an inner surface configured to cooperate with a user's face to define an interior space therebetween, and two straps respectively connected to two opposite sides of the mask body. The container has a container body defining a chamber for receiving working liquid and formed with a plurality of vent holes for communicating the chamber with the interior space. At least one gas generating unit is connected to the container, and includes an electrolysis device disposed in a casing thereof for electrolyzing the working liquid into a hydrogen/oxygen gas mixture.

9 Claims, 6 Drawing Sheets

BREATHING MASK

CROSS-REFERENCE TO RELATED APPLICATION

This application claims priority to Taiwanese Patent Application No. 108121081, filed on Jun. 18, 2019.

FIELD

The disclosure relates to a mask, more particularly to a breathing mask that provides a hydrogen/oxygen gas mixture.

BACKGROUND

The air pollution problem has gradually attracted public attention in recent years, and how to fight the invisible pollution has become a major issue. The masks on the market claimed to be resistant to fine suspended particles in the air mostly use a single layer or multi-layer filter material to achieve the effect of filtering the air.

Since the sizes of the fine suspended particles are too small, the pore sizes of the aforesaid filter material must also be made smaller in order to filter out the fine suspended particles. However, the smaller the diameters of the pores of the filter material, the more difficult it is for the air to pass through, so that a user initially wearing this type of mask will find difficulty in breathing. Even if he/she can breathe clean air, the quality of breathing is still affected to some extent.

SUMMARY

Therefore, an object of the present disclosure is to provide a breathing mask that can alleviate at least one of the drawbacks of the prior art.

Accordingly, a breathing mask of this disclosure includes a mask body unit, a container, and at least one gas generating unit. The mask body unit includes a mask body suitable for covering at least the nose of a user, and two straps respectively connected to two opposite sides of the mask body. The mask body has an inner surface configured to cooperate with the user's face to define an interior space therebetween, and an outer surface opposite to the inner surface. The container is disposed on the inner surface of the mask body, and has a container body that defines a chamber for receiving working liquid and that is formed with a plurality of vent holes at a top side thereof for communicating the chamber with the interior space. The at least one gas generating unit is connected to the container, and includes a casing, an electrolysis device disposed in the casing for electrolyzing the working liquid into a hydrogen/oxygen gas mixture, a control member for controlling the operation of the electrolysis device, and a power source electrically connected to the electrolysis device and the control member.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Before the present disclosure is described in greater detail with reference to the accompanying embodiments, it should be noted herein that like elements are denoted by the same reference numerals throughout the disclosure.

Figure 1:
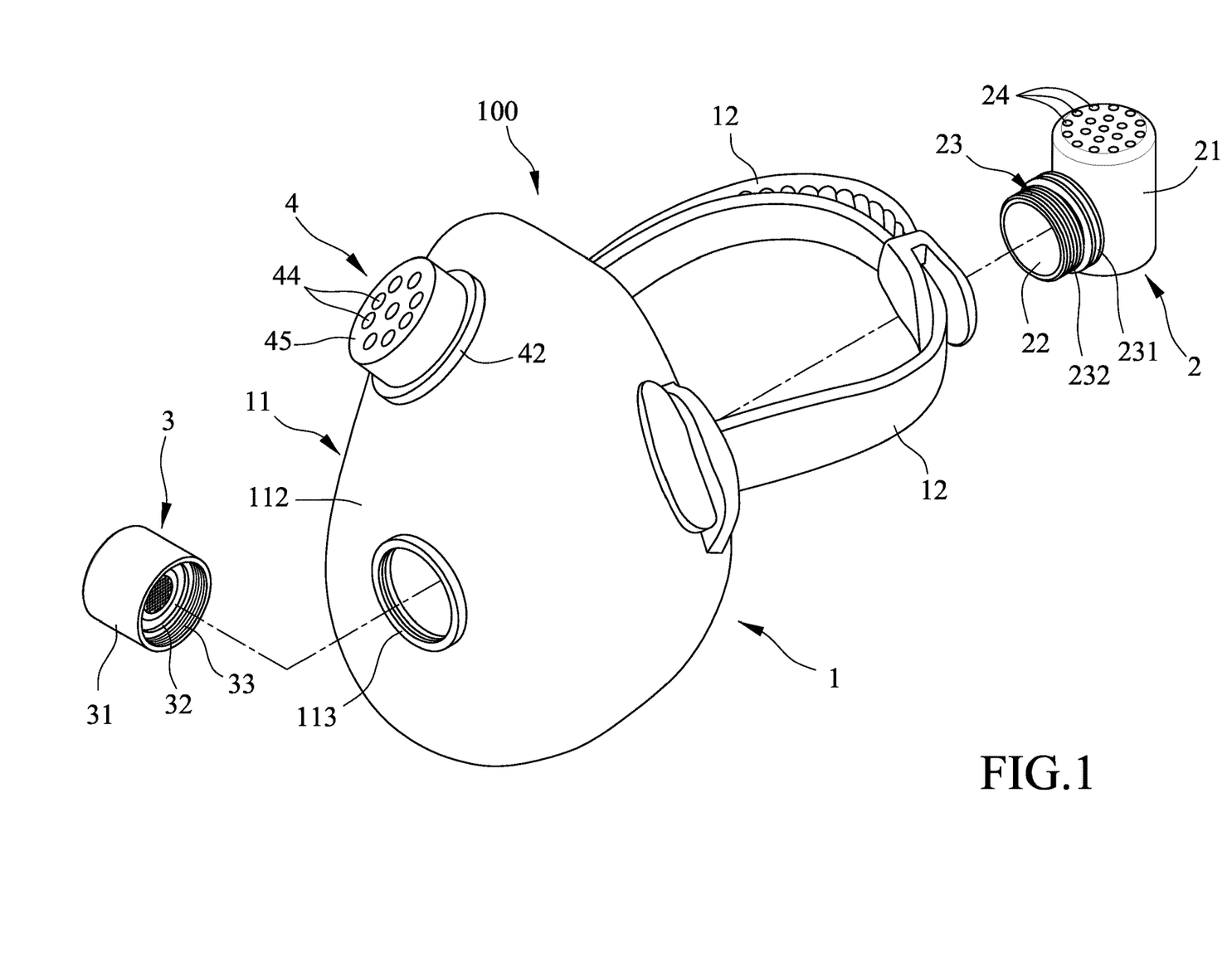
FIG. 1 is a partially exploded perspective view of a breathing mask according to the first embodiment of the present disclosure.
Figure 2:
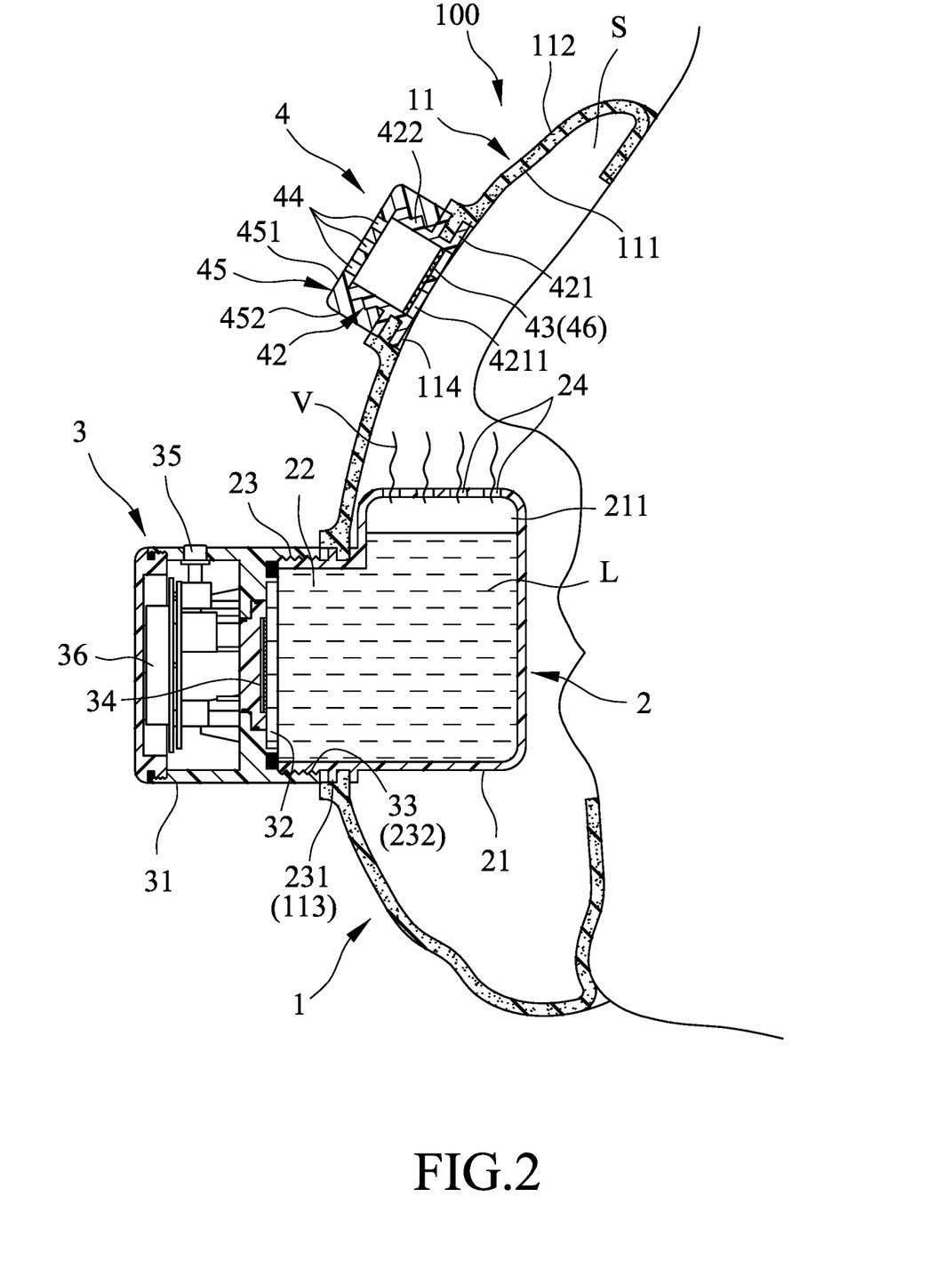
FIG. 2 is an assembled sectional view of the first embodiment in a state of use.

Referring to FIGS. 1 and 2, a breathing mask 100 according to the first embodiment of the present disclosure includes a mask body unit 1, a container 2, a gas generating unit 3 and an air regulating unit 4.

The mask body unit 1 includes a mask body 11 configured to cover a user's nose and mouth, and two straps 12 respectively connected to two opposite sides of the mask body 11 for supporting the mask body 11 over the user's nose and mouth. In this embodiment, one of the straps 12 is adjustably connected to the other strap 12 by inserting one end thereof into a connecting member 121 of the other strap 12 and positioned thereat through a rack of teeth on an inner surface of the other strap 12. The mask body 11 has an inner surface 111 for facing the user's face and for cooperating with the same to define an interior space (S) therebetween, an outer surface 112 opposite to the inner surface 111, a threaded hole 113 extending through the inner and outer surfaces 111, 112, and an insertion hole 114 extending through the inner and outer surfaces 111, 112 and spaced apart from the threaded hole 113. The mask body 11 is made from one of plastic, silicone and rubber or a combination thereof to effectively block external polluted air and to have sufficient structural strength for supporting the container 2 and the gas generating unit 3 when they are mounted thereto. In an alternative embodiment, the straps 12 may be elastic bands that extend around the ears to achieve a fixing effect, or silicone straps that extend around the head to achieve a fixing effect, as long as the mask body 11 can be fixed over the user's nose and mouth so as to cover the same, any form of straps is acceptable.

The container 2 is disposed on the inner surface 111 of the mask body 11, and has a container body 21 defining a chamber 211 for receiving working liquid (L). The container body 21 is formed with a plurality of vent holes 24 at a top side thereof for communicating the chamber 211 with the interior space (S), and has a first connecting portion 23 provided at one side of an outer peripheral surface thereof and extending away from the user. The first connecting portion 23 defines a first passage 22 communicating with the chamber 211, and has an outer peripheral surface formed with a first external thread 231 adjacent to the outer peripheral surface of the container body 21, and a second external thread 232 opposite to the first external thread 231. It is worth to mention herein that the working liquid (L) contained in the chamber 211 is one of pure water, distilled water, and mineral water.

The gas generating unit 3 includes a casing 31 having a second connecting portion 33 formed at one end thereof and defining a second passage 32 for communicating with the first passage 22, an electrolysis device 34 disposed in the casing 31 for electrolyzing the working liquid (L) into a hydrogen/oxygen gas mixture (V), a control member 35 disposed in the casing 31 for controlling the operation of the electrolysis device 34, and a power source 36 disposed in the casing 31 and electrically connected to the electrolysis device 34 and the control member 35. The second connecting portion 33 has an internal thread for threaded engagement with the second external thread 232 of the first connecting portion 23. The power source 36 is a battery capable of storing and supplying electric energy.

The air regulating unit 4 includes an exhaust member 42, a regulating member 43 and a cover member 45. The exhaust member 42 includes a head 421 fitted in the insertion hole 114 of the mask body 11 and having an exhaust hole 4211 communicating with the interior space (S), and a tubular portion 422 extending outwardly from the head 421 and having an external thread. The cover member 45 is removably covered on the exhaust member 42, and includes an end wall 451 formed with a plurality of air inlets 44, and a peripheral wall 452 extending outwardly from an outer periphery of the end wall 451 and having an internal thread threadedly connected to the external thread of the tubular portion 422.

During assembly, the container body 21 is first connected to the mask body 11 by inserting the first connecting portion 23 through the threaded hole 113 and threadedly connecting the first external thread 231 thereof with the threaded hole 113 such that the second external thread 232 thereof is exposed on the outer surface 112 of the mask body 11, after which the second connecting portion 33 of the casing 31 of the gas generating unit 3 is threadedly connected to the second external thread 232 of the first connecting portion 23. At this time, the container 2 and the gas generating unit 3 are fixed to the mask body 11 with the container body 21 being positioned under the user's nose, and the exhaust member 42 is spaced apart from the assembly of the container 2 and the gas generating unit 3.

In use, the working liquid (L) is first poured into the chamber 211 of the container body 21, after which the first external thread 231 of the first connecting portion 23 is threadedly connected to the threaded hole 113 in the mask body 11 and the second connecting portion 33 is threadedly connected to the second external thread 232 of the first connection portion 23. Through this, the working liquid (L) can flow from the first passage 22 to the gas generating unit 3 through the second passage 32. The breathing mask 100 is then positioned on the user's head through the straps 12 and with the mask body 11 covering the user's nose and mouth. Next, the control member 35 is activated to control the electrolysis device 34 to form positive and negative electrodes that generate an electric current passing through and electrolyzing the working liquid (L) to produce a hydrogen/oxygen gas mixture (V). Since the hydrogen/oxygen gas mixture (V) has low density, it will flow upward and pass through the vent holes 24 for direct inhalation by the user.

When the liquid level of the working liquid (L) gradually decreases with use, the container 2 is first separated from the gas generating unit 3, after which it is detached from the mask body 1, so that the container body 21 can be refilled with the working liquid (L), and the breathing mask 100 can be used again to generate the hydrogen/oxygen gas mixture (V). In comparison with the existing mask which may accumulate dirt over time and which must be discarded and replaced with a new one, the breathing mask 100 of this embodiment can be repeatedly used.

Moreover, considering that the mask body 11 covers the user's nose and mouth and limits the exhalation of air therefrom, air pressure inside the interior space (S) may gradually increase under prolonged use. To resolve this problem and without affecting the effectiveness of providing clean air, the regulating member 43 of the first embodiment is configured as a filter screen 46. The filter screen 46 is disposed adjacent to and outwardly of the exhaust hole 4211 so as to removably cover the same. The cover member 45 covers the exhaust member 42 and the filter screen 46. Through this, even if an external polluted air enters the air regulating unit 4 through the air inlets 44 of the cover member 45, it will be filtered out by fine pore diameters on the surface of the filter screen 46, so that the purity of air entering the air regulating unit 4 is ensured. On the other hand, the gas exhaled by the user will flow out through the exhaust hole 4211 according to the law of diffusion, thereby achieving the effect of regulating the internal air pressure without affecting the effect of blocking the external polluted air.

Oxygen is a substance necessary for the human body to maintain cell operation. Inhaling oxygen can make the circulation of various functions in the human body smoother, and achieve the effects of eliminating fatigue, environmental protection in the body, improving learning ability, and improving memorization. On the other hand, hydrogen is an anti-oxidant substance which can slow down the aging of various parts of the human body, and can achieve the effects of restoring skin elasticity and reducing wrinkles. Since any part of the human body may produce free radicals looking for electron neutralization, and when the free radicals and the cells and proteins in the human body produce an electronic neutralization reaction, an oxidation reaction occurs, and oxidized lipids are accumulated, thereby affecting the normal operation of the human body. Because hydrogen is a reducing agent in the reduction-oxidation reaction and can bind to the free radicals in the human body, it can prevent accumulation of oxidized lipids in the body, thereby achieving detoxification and purification effects. Moreover, inhalation of hydrogen can also achieve faster recovery of body damage, so that it has a healing effect.

Figure 3:
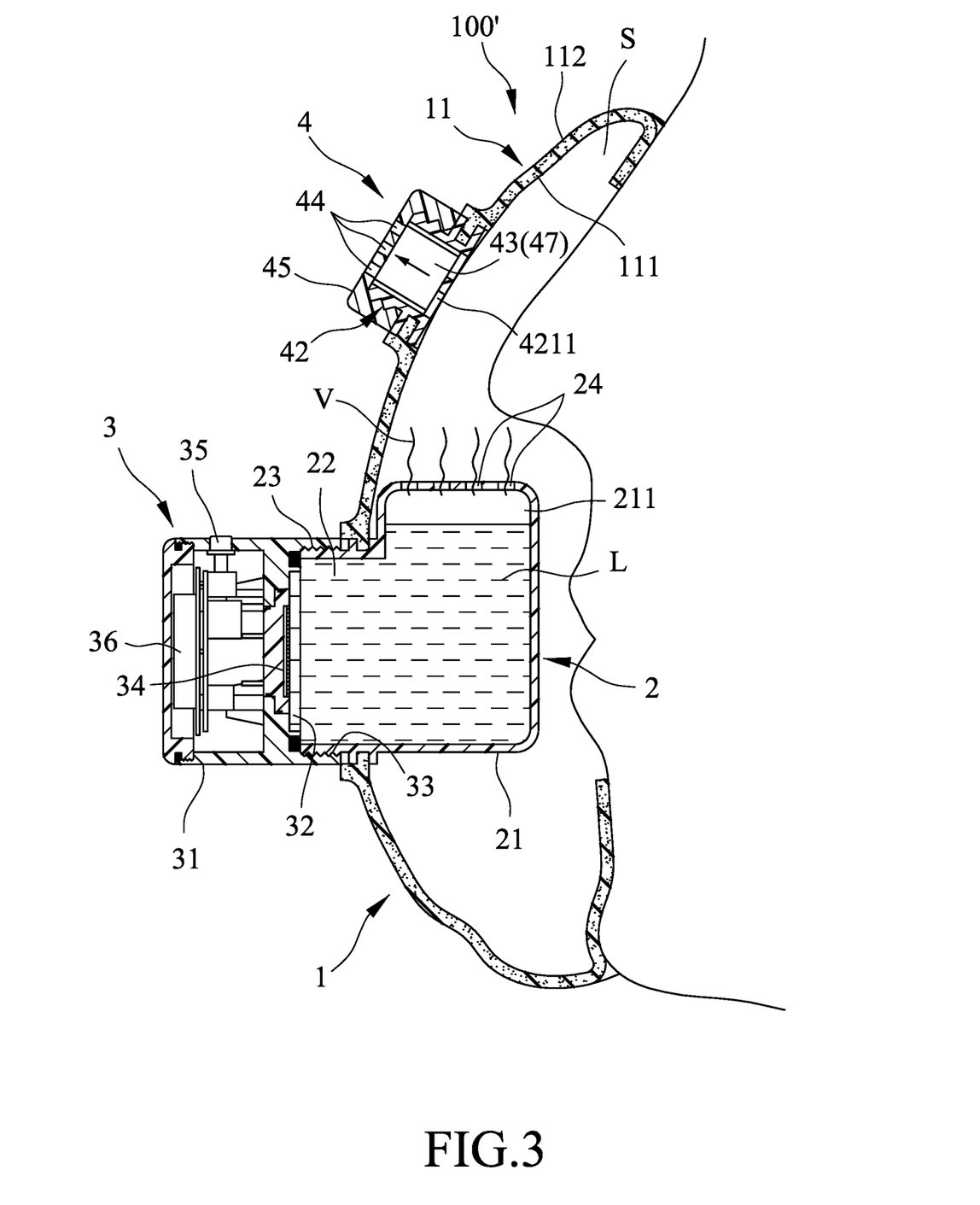
FIG. 3 is an assembled sectional view of a breathing mask according to the second embodiment of the present disclosure.

Referring to FIG. 3, the second embodiment of the breathing mask 100' according to this disclosure is shown to be identical to the first embodiment. However, in the second embodiment, the regulating member 43 of the air regulating unit 4 of the second embodiment is configured as a one-way air valve 47 disposed adjacent to and outwardly of the exhaust hole 4211 for only allowing air in the interior space (S) to discharge outwardly. Through the characteristics of the one-way air valve 47 that restricts the flow direction of the air, the inflow of the external polluted air is restricted, and a duct for exhaust of internal air is provided. The second embodiment can achieve effects similar to those described in the first embodiment.

Figure 4:
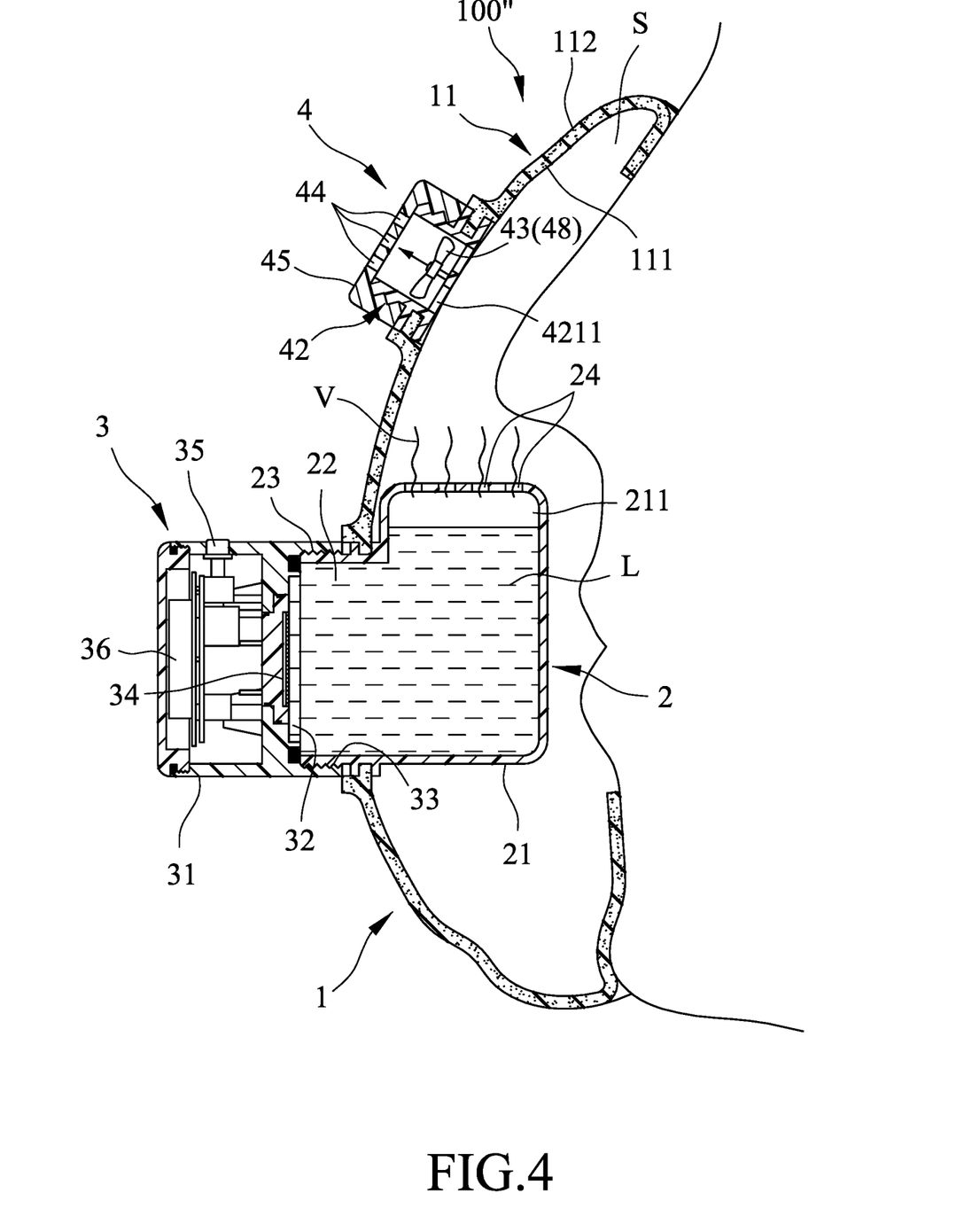
FIG. 4 is an assembled sectional view of a breathing mask according to the third embodiment of the present disclosure.

Referring to FIG. 4, the third embodiment of the breathing mask 100'' according to this disclosure is shown to be identical to the first embodiment. However, in the third embodiment, the regulating member 43 is configured as a fan 48 disposed adjacent to and outwardly of the exhaust hole 4211 and electrically connected to the power source 36 for discharging the air in the interior space (S) outwardly. By using the fan 48 to regulate the air pressure in the interior space (S) and to restrict the inflow of external polluted air, the third embodiment can achieve effects similar to those described in the first embodiment.

Figure 5:
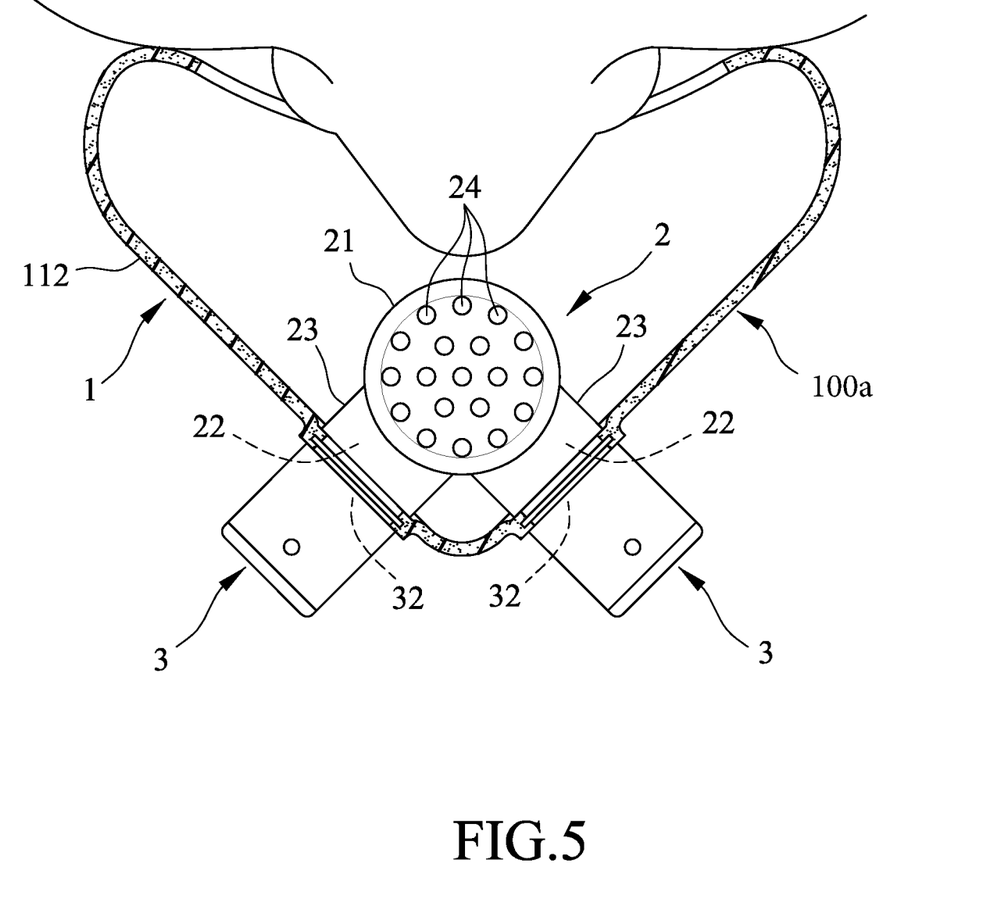
FIG. 5 is an assembled sectional view of a breathing mask according to the fourth embodiment of the present disclosure.

Referring to FIG. 5, the fourth embodiment of the breathing mask (100a) according to this disclosure is shown to be identical to the first embodiment. However, in the fourth embodiment, the container body 21 of the container 2 has two first connecting portions 23 provided on the outer peripheral surface thereof and angularly spaced apart from each other, and the breathing mask (100a) comprises two gas generating units 3 respectively connected to the first connecting portions 23 for increasing the efficiency of producing hydrogen and oxygen gases. The working liquid (L) (not shown) can flow to the gas generating units 3 through the first passages 22 and the second passages 32, and is electrolyzed to produce a hydrogen/oxygen gas mixture (V) (not shown) that flows upward and pass through the vent holes 24 for direct inhalation by the user. The effect of increasing the production of hydrogen and oxygen gases can thus be achieved.

Figure 6:
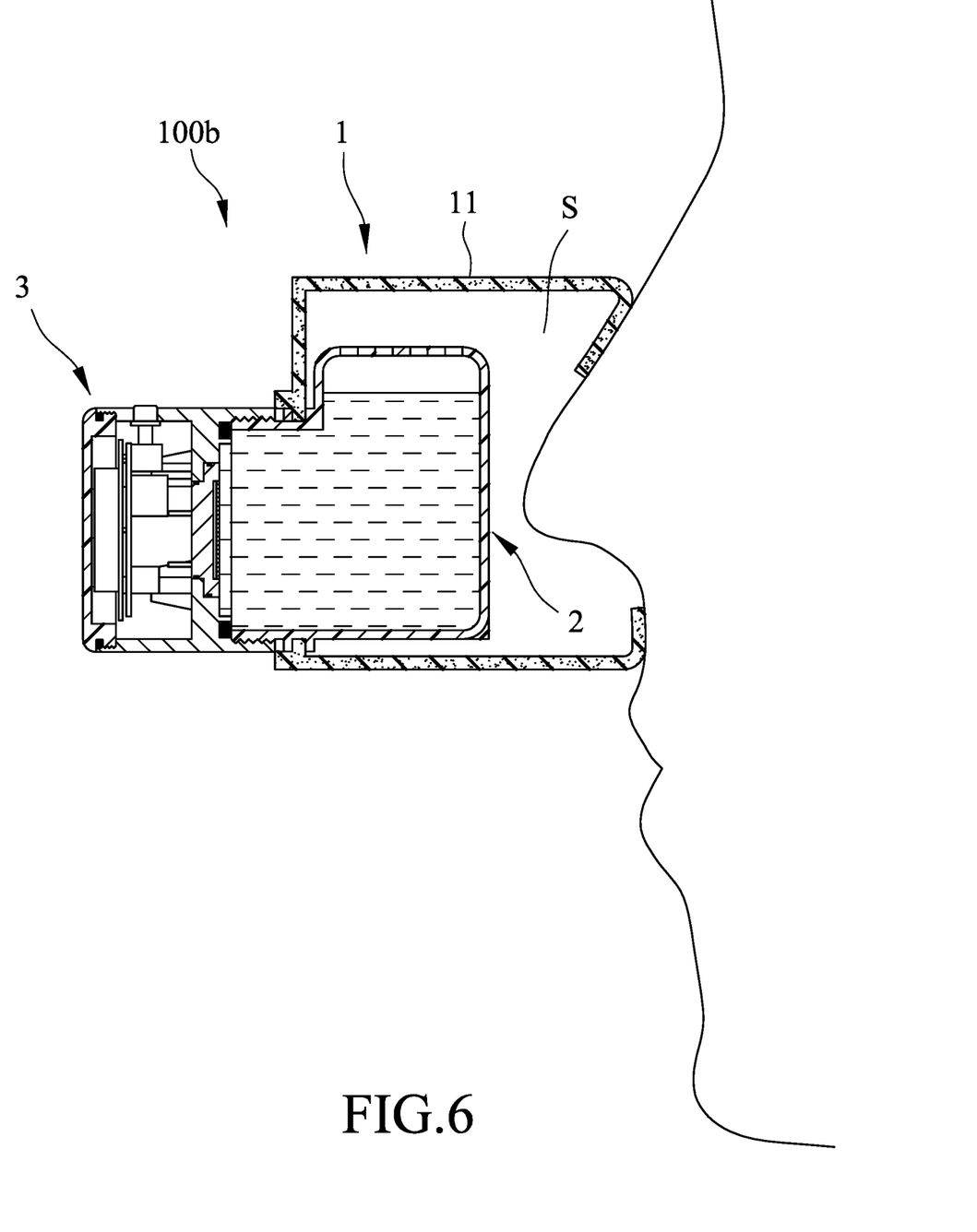
FIG. 6 is an assembled sectional view of a breathing mask according to the fifth embodiment of the present disclosure.

Referring to FIG. 6, the fifth embodiment of the breathing mask (100b) according to this disclosure is shown to be different from the aforesaid embodiments in that, in the fifth embodiment, the mask body 11 of the mask body unit 1 only covers the user's nose. Since the user can inhale through the nose and exhale from the mouth, the air pressure in the interior space (S) of the mask body unit 1 will not continue to rise, so that there is no need to provide the air regulating unit 4 in this case. Thus, the volume of the overall structure of the breathing mask (100b) is reduced, so that it is easy to carry the breathing mask (100b).

In summary, in the breathing mask 100, 100', 100", 100a, 100b of this disclosure, through the connection of the first connecting portion 23 and the second connecting portion 33, the gas generating unit 3 and the container unit 2 can be connected to each other and can be positioned on the mask body 21. Further, after the working liquid (L) is electrolyzed to produce the hydrogen/oxygen gas mixture (V), because the hydrogen/oxygen gas mixture (V) has low density, it will flow upward and pass through the vent holes 24 for direct inhalation by the user. During use, the mask body unit 1 blocks most of the external polluted air, the gas generating unit 3 continuously supplies fresh hydrogen/oxygen gas mixture (V) to the user, and with the air pressure regulation of the air regulating unit 4, the effect of actively providing clean air is achieved. Therefore, the object of this disclosure can indeed be achieved.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A breathing mask, comprising:
    a mask body unit including a mask body suitable for covering at least the nose of a user, and two straps respectively connected to two opposite sides of said mask body, said mask body having an inner surface configured to cooperate with the user's face to define an interior space therebetween, and an outer surface opposite to said inner surface;
    a container disposed on said inner surface of said mask body and having a container body that defines a chamber for receiving working liquid, said container body being formed with a plurality of vent holes at a top side thereof for communicating said chamber with said interior space; and
    at least one gas generating unit connected to said container and including a casing, an electrolysis device disposed in said casing for electrolyzing the working liquid into a hydrogen/oxygen gas mixture, a control member for controlling an operation of said electrolysis device, and a power source electrically connected to said electrolysis device and said control member;
    wherein said container body has at least one first connecting portion provided at one side of an outer peripheral surface thereof and extending away from the user, said at least one first connecting portion defining a first passage communicating with said chamber, said casing having a second connecting portion connected to said first connecting portion and defining a second passage communicating with said first passage.

2. The breathing mask as claimed in claim 1, wherein the working liquid contained in said chamber is one of pure water, distilled water, and mineral water.

3. The breathing mask as claimed in claim 1, wherein said mask body is made from one of plastic, silicone, rubber, and a combination thereof.

4. The breathing mask as claimed in claim 1, wherein said at least one first connecting portion and said second connecting portion are threadedly connected to each other.

5. The breathing mask as claimed in claim 1, further comprising an air regulating unit which includes an exhaust member connected to said mask body and spaced apart from an assembly of said container and said at least one gas generating unit, a regulating member suitable for regulating air in said interior space, and a cover member removably covering said exhaust member and having a plurality of air inlets, said exhaust member having an exhaust hole communicating with said interior space.

6. The breathing mask as claimed in claim 5, wherein said regulating member is configured as a filter screen removably covering said exhaust hole.

7. The breathing mask as claimed in claim 5, wherein said regulating member is configured as a one-way air valve disposed adjacent to and outwardly of said exhaust hole for only allowing air in said interior space to discharge outwardly.

8. The breathing mask as claimed in claim 5, wherein said regulating member is configured as a fan disposed adjacent to and outwardly of said exhaust hole and electrically connected to said power source for discharging air in said interior space outwardly.

9. The breathing mask as claimed in claim 1, wherein said container body has two said first connecting portions provided on said outer peripheral surface thereof and angularly spaced apart from each other, and said breathing mask comprises two said gas generating units respectively connected to said first connecting portions.

* * * * *